United States Patent
Huber et al.

(10) Patent No.: US 8,436,209 B2
(45) Date of Patent: May 7, 2013

(54) PROCESS FOR THE MANUFACTURE OF MEMANTINE AND INTERMEDIATE PRODUCT

(75) Inventors: Florian Anton Martin Huber, Bozen (IT); Giorgio Gallo, Salboro (IT); Carla De Faveri, Farra di Sloigo (IT)

(73) Assignee: Merz Pharma GmbH & Co. KGaA, Frankurt am Main (DE)

( * ) Notice: Subject to any disclaimer, the term of this patent is extended or adjusted under 35 U.S.C. 154(b) by 301 days.

(21) Appl. No.: 12/736,198

(22) PCT Filed: Mar. 19, 2009

(86) PCT No.: PCT/EP2009/002049
§ 371 (c)(1),
(2), (4) Date: Dec. 3, 2010

(87) PCT Pub. No.: WO2009/115334
PCT Pub. Date: Sep. 24, 2009

(65) Prior Publication Data
US 2011/0082317 A1    Apr. 7, 2011

Related U.S. Application Data

(60) Provisional application No. 61/070,246, filed on Mar. 20, 2008.

(30) Foreign Application Priority Data

Mar. 20, 2008 (EP) .................................... 08005371
Nov. 21, 2008 (EP) .................................... 08020340

(51) Int. Cl.
*C07C 231/08* (2006.01)
*C07C 233/57* (2006.01)

(52) U.S. Cl.
USPC ........................................ 564/217; 564/459

(58) Field of Classification Search .................. 564/217, 564/459
See application file for complete search history.

(56) References Cited

U.S. PATENT DOCUMENTS 5,061,703  A    10/1991  Bormann et al.
8,138,375  B2 *  3/2012  Schreiner et al. ............. 564/222

FOREIGN PATENT DOCUMENTS

| DE | 10 2008 009279 | 3/2008 |
| RU | 2309940 | 11/2007 |
| SU | 408546 | 12/1976 |
| WO | WO 2006/010362 | 2/2006 |
| WO | WO 2006/048750 | 5/2006 |
| WO | WO/2007/101536 | 9/2007 |

OTHER PUBLICATIONS

European Search Report for EP08005371 of Oct. 22, 2008.
International search Report with Written Opinion for PCT/EP2009/002049 of Sep. 10, 2009.
Wanka, et al., "γ-Aminoadamantanecarboxylic acids through direct C-H bond amidations" Eur. J. Org. Chem. p. 1474-1490, 2007.
Yu N Klimochkin, et al., "Synthesis of alkyxycarbonylaminoadamantanes and acetylaminoadamantanes in nitric acid" Bulletin Fo the Academy of Sciences of the USSR, vol. 37, No. 4, p. 757-759, Jan. 1, 1988.
U.S. Appl. No. 12/224,575, filed Jan. 12, 2009.

* cited by examiner

*Primary Examiner* — Shailendra Kumar
(74) *Attorney, Agent, or Firm* — Hueschen and Sage

(57) ABSTRACT

The present invention relates to a process for manufacturing N-Formyl-1-amino-3,5-dimethyladamantane, an intermediate product in the overall process of producing 1-Amino-3,5-dimethyladamantane hydrochloride (Memantine). Therein, the process comprises the following steps:

(a) reacting 1,3-dimethyladamantane with an acid mixture comprising concentrated sulfuric acid and concentrated nitric acid, wherein 1 to 6 volume parts of sulfuric acid (measured in ml) are used per weight part of 1,3-dimethyladamantane (measured in g);

(b) reacting the solution from step (a) with an amount of formamide varying from 1 to 5 molar equivalents per mole of deprotonated 1,3-dimethyladamantane from step (a) to obtain N-Formyl-1-amino-3,5-dimethyladamantane.

In step (b), the molar ratio of total acid, i.e. the molar amount of sulfuric acid and the molar amount of nitric acid taken together versus the molar amount of formamide is at least 1.5 and that the temperature is at least 50° C. The present invention also relates to the overall process of manufacturing Memantine from 1,3-dimethyladamantane by means of hydrolyzing the intermediate NFORM.

14 Claims, 2 Drawing Sheets

US 8,436,209 B2

PROCESS FOR THE MANUFACTURE OF MEMANTINE AND INTERMEDIATE PRODUCT

This application is a 371 of PCT/EP2009/002049, filed on Mar. 19, 2009, which claims benefit of 61/070,246 Mar. 20, 2008.

FIELD OF THE INVENTION

The present invention relates to a process for manufacturing N-Formyl-1-amino-3,5-dimethyladamantane (in the following: "NFORM"), an intermediate product in the overall process of producing 1-Amino-3,5-dimethyladamantane hydrochloride (Memantine hydrochloride, Memantine HCl; in the following "Memantine").

In accordance with the present invention, the process for the manufacture of N-Formyl-1-amino-3,5-dimethyladamantane comprises the following steps:

(a) reacting 1,3-dimethyladamantane with an acid mixture comprising concentrated sulfuric acid and concentrated nitric acid, wherein 1 to 6 volume parts of sulfuric acid (measured in ml) are used per weight part of 1,3-dimethyladamantane (measured in g);

(b) reacting the solution from step (a) with an amount of formamide varying from 1 to 5 molar equivalents per mole of deprotonated 1,3-dimethyladamantane from step (a) to obtain N-Formyl-1-amino-3,5-dimethyladamantane.

In accordance with the present invention, in step (b), the molar ratio of total acid, i.e. the molar amount of sulfuric acid and the molar amount of nitric acid taken together versus the molar amount of formamide is at least 1.5.

In a further embodiment, the ratio of total acid versus formamide in step (b) is in a range of 2:1 to 5:1.

According to a further embodiment, in step (b) the temperature is at least 50° C. In accordance with a further embodiment, said temperature is between 50-65° C.

The present invention also relates to the overall process of manufacturing Memantine from 1,3-dimethyladamantane comprising the further step (c) of hydrolyzing the intermediate NFORM from steps (a) and (b).

Memantine is a moderate affinity NMDA-receptor antagonist and used as a medicament to treat various diseases, in particular moderate to severe Alzheimer's disease and glaucoma. Memantine is also being tested and possibly indicated for treating Opioid dependence, systemic lupus erythematosus, depression, obsessive compulsive disorder, tinnitus, neuropathic pain and pervasive developmental disorders. Memantine manufactured in accordance with the inventive process can be used for any of these and all other conceivable indications.

BACKGROUND OF THE INVENTION

U.S. Pat. No. 5,061,703 discloses a general method for the preparation of aminoalkyladamantanes. The synthesis comprises three steps: halogenation of alkyladamantanes with elemental chlorine or bromine; formylation of the halogenated alkyladamantanes with formamide. The final acid hydrolysis gives a range of aminoalkyladamantanes.

This method employs hazardous and toxic reagents (in particular chlorine or bromine) and the synthesis typically requires a large excess of the key reagents. This generates a considerable amount of waste, which is not desirable, among others, from an environmental and an economic point of view.

Another method for the direct preparation of N-Formyl-1-amino-3,5-dimethyladamantane from 1,3-dimethyladamantane (1,3-DMA) using strong acids and formamide was described by L. Wanka, C. Cabrele, M. Vanejews, and P. R. Schreiner in Eur. J. Org. Chem. 2007, 1474-1490.

A similar process is disclosed in WO 2007/101536 A1. However, the process described in these publications still has several drawbacks. Although the process avoids the use of elemental bromine, the overall process still results in considerable waste as it employs a large excess of formamide (63 molar equivalents), sulphuric acid (22 molar equivalents, 8 volume parts per weight part of 1,3-DMA), and nitric acid (1.8 molar equivalents), all of which need to be disposed and/or carried through the working-up procedure. Besides, a large amount of halogenated organic solvents must be used in said process in order to extract the product from the mixture. Furthermore an additional purification step by chromatography is reported, which may not be economically viable on the industrial scale.

SUMMARY OF THE INVENTION

In light of the prior art on record, it is one objective of the present invention to provide an improved process for manufacturing N-Formyl-1-amino-3,5-dimethyladamantane (also known as 1-Formamido-3,5-dimethyltricyclo[3.3.1.1.$^{3,7}$]decane and designated in the following "NFORM") starting from 1,3-dimethyladamantane (in the following "1,3-DMA") that avoids or minimizes any of the above-mentioned problems, in particular the use of hazardous chemicals. According to a further object, the process does not involve a halogenation step.

It is in another object to minimize the amount of waste and/or unused chemicals produced during the manufacture of Memantine or its intermediate products. It is a further object to optimize or improve the yield and/or selectivity and/or product quality in regard to Memantine or its intermediate products.

According to another object, the improved yield/selectivity/quality of product should particularly be visible in the process for manufacturing Memantine as scaled-up to a commercial/industrial use, i.e. involving batches on the kilogram scale or on the hundreds of kilograms scale.

These objects and other objects are solved by a process for the manufacture of N-Formyl-1-amino-3,5-dimethyladamantane comprising the following steps:

(a) reacting 1,3-dimethyladamantane with an acid mixture comprising concentrated sulfuric acid and concentrated nitric acid, wherein 1 to 6 volume parts of sulfuric acid (measured in ml) are used per weight part of 1,3-dimethyladamantane (measured in g);

(b) reacting the solution from step (a) with an amount of formamide varying from 1 to 5 molar equivalents per mole of deprotonated 1,3-dimethyladamantane from step (a) to obtain N-Formyl-1-amino-3,5-dimethyladamantane.

In accordance with the present invention, in step (b), the molar ratio of total acid, i.e. the molar amount of sulfuric acid and the molar amount of nitric acid taken together versus the molar amount of formamide is at least 1.5. According to a further embodiment, the ratio of total acid versus formamide is in a range of 2:1 to 5:1.

In accordance with another embodiment of the invention, in step (b) the temperature is at least 50° C., in an alternative embodiment in a range from 50° C. to 65° C.

DETAILED DESCRIPTION OF THE INVENTION

Figure 1:
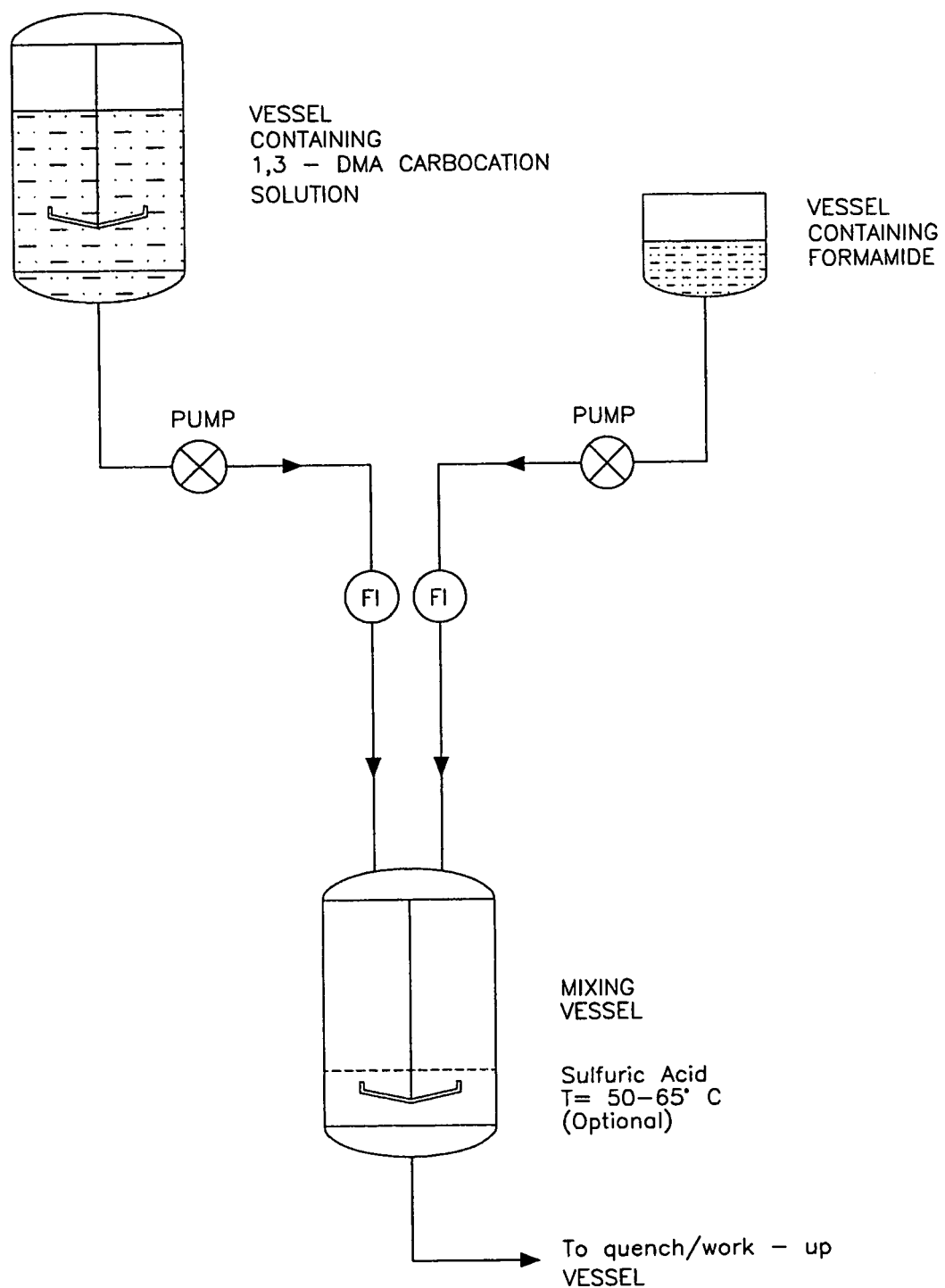
FIG. 1 shows an embodiment in accordance with the present invention, wherein the 1,3-DMA carbocation solution and the formamide are concurrently added to a mixing vessel (batch modus).

The present invention relates to a process for the preparation of NFORM feasible to be performed on an industrial scale.

The present invention comprises two steps: In a first step, step (a), 1,3-DMA is reacted with concentrated sulfuric acid and nitric acid. Without wishing to be bound by any theory or mechanism, this step is meant to create the carbocation of 1,3-DMA. In a second step, step (b), the carbocation of 1,3-DMA is reacted with formamide to give NFORM.

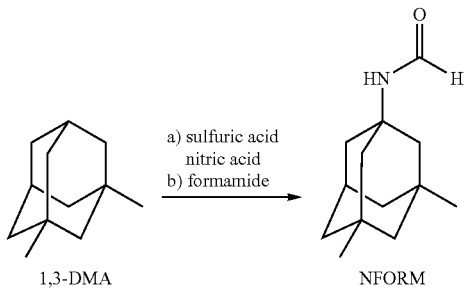

In the following, a detailed description of particular embodiments in regard to step (a) and step (b) are given.

Step (a): Concentration of Sulfuric Acid and Nitric Acid

In accordance with one embodiment, the concentrated sulfuric acid is used in a concentration range of 90% to 98% by weight, furthermore 94% to 98% by weight.

In a further embodiment, the concentrated nitric acid is used in a concentration range of 60% to 70% by weight, furthermore 65% to 70% by weight.

In the process for manufacturing NFORM, the presence of a certain amount of water, be it from the acid employed in step (a) or be it from any other source, is not detrimental to the conversion of the 1,3-DMA into the carbocation. Therefore the process according to the present invention allows to avoid the use of oleum and anhydrous acids.

Step (a): Temperature

In one embodiment of the invention, step (a) is performed at temperatures from −10° C. to 50° C. and, in a further embodiment, at temperatures from 0° C. to 10° C.

Step (a): Ratio of Sulfuric Acid Vs. 1,3-DMA

In accordance with the present invention, the excess of sulfuric acid versus the starting material 1,3-DMA should be reduced to minimize the amount of acidic waste in the process. In accordance with the present invention, 1 to 6 volume parts of sulfuric acid as measured in ml (per weight part of 1,3-dimethyladamantane as measured in g) are used.

In a further embodiment, 3 to 5 volume parts of sulfuric acid (as measured in ml) are used per weight part of 1,3-DMA (as measured in g).

Without wishing to be bound to a specific functional understanding, the sulfuric acid is seen as functioning both as solvent and reagent in step (a).

On the laboratory scale, the specific mode of mixing of the three components is not critical, however, on an industrial scale, for safety reasons, slow addition of the nitric acid into a vigorously stirred biphasic mixture of 1,3-DMA/sulfuric acid is employed.

Step (a): Ratio of Nitric Acid Vs. 1,3-DMA

According to one embodiment of the present invention, nitric acid is used in a range from 0.5 to 2 molar equivalents (versus one molar equivalent of 1,3-dimethyladamantane). In a further embodiment, a range of 0.6 to 0.8 molar equivalents of nitric acid per molar equivalent of 1,3-DMA is employed.

In accordance with the present invention, in the second step, step (b), formamide is reacted with the solution of step (a). Without wishing to be bound to any theory or mechanism, it is believed that in this step, nucleophilic formamide attacks the carbocation created in step (a) thus leading to the desired intermediate product NFORM.

Step (b): Molar Ratio of Formamide (Reagent) Vs. 1,3-DMA-Carbocation from Step (a)

The procedure disclosed in the prior art (for example in WO 2007/101536) entails the mixing of deprotonated 1,3-DMA with a large excess of formamide, namely 63 molar equivalents. Typically, when a process is performed on industrial scale, parameters such as temperature and rate of addition of reagents (dose control) are fundamental for safety and quality/regulatory aspects. However, applying the procedure of the prior art scrupulously using the stated excess of formamide, controlling the temperature strictly and using a controlled addition rate of reagents (as required on industrial scale), only a low conversion of 1,3-DMA into NFORM was observed.

In contrast to the teaching of the prior art and in accordance with the present invention, either a stoichiometric amount of formamide versus the amount of deprotonated 1,3-DMA (i.e. the 1,3-DMA carbocation) or only a small excess of formamide is employed.

According to one embodiment, the amount of formamide employed ranges from 1 to 5 molar equivalents.

According to a further embodiment of the invention, 1.5 to 3 molar equivalents of form amide are employed.

Reducing the amount of formamide used in the formylation step (b) is not only desirable from an environmental point of view but also has been found to surprisingly improve the conversion of the carbocation into the intermediate product NFORM, and as a consequence, the overall conversion of 1,3-DMA into Memantine HCl. Furthermore, if the amount of excess of formamide is minimized, the working-up steps are facilitated.

Step (b): Molar Ratio of Total Acid Vs. Formamide

In addition to the relevance of the ratio of formamide versus 1,3-DMA carbocation, it was found that the ratio of the molar amount of "acid" versus formamide is of importance for the NFORM formation.

Therein, the term "acid" is meant to be the molar amount of sulfuric acid plus the molar amount of nitric acid ("total acid").

The molar ratio of total acid versus formamide needs to be at least 1.5 to lead to a sufficient conversion of 1,3-DMA into NFORM (N-Formyl-1-amino-3,5-dimethyladamantane). Otherwise, it has been found that predominantly unwanted side products such as 1-hydroxy-3,5-dimethyladamantane and O-formyl-1-oxy-3,5-dimethyladamantane are formed.

According to one embodiment of the invention, the ratio of total acid versus formamide is in the range of 2 to 5. The prior art process described in WO 2007/101536 instead uses acid in deficiency.

Step (b): Formylation Temperature

The reaction temperature of the formylation reaction (carbocation reaction with form amide) of step (b) is also a relevant parameter. According to one embodiment of the present invention, a temperature of at least 50° C. is employed to form the intermediate NFORM. It is believed that below this temperature, predominantly 1-hydroxy-3,5-dimethyladamantane and O-formyl-1-oxy-3,5-dimethyladamantane are formed:

According to one embodiment of this invention, the temperature is maintained at 50° C. to 65° C. during the mixing stage. Higher reaction temperatures (above 70° C.) may lead to the formation of impurities.

Step (B): Mode of Mixing

The mixing of the carbocation with the formamide in step (b) may be performed in at least three different modes: (i) addition of formamide to the carbocation, (ii) addition of the carbocation to formamide or, as a third option, (iii) simultaneous (concurrent) mixing of the two components. It was found that the first two modes, do lead to product formation but also lead to unwanted side reactions at the required temperatures.

Without wishing to be bound by theories or mechanisms, it would seem that the carbocation solution may (partially) decompose into impurities when heated for a prolonged time while the formamide is being added [addition mode (i)]. Also, the formamide may decompose to carbon monoxide and ammonia if the acidic carbocation is added slowly onto the formamide [addition mode (ii)].

Figure 2:
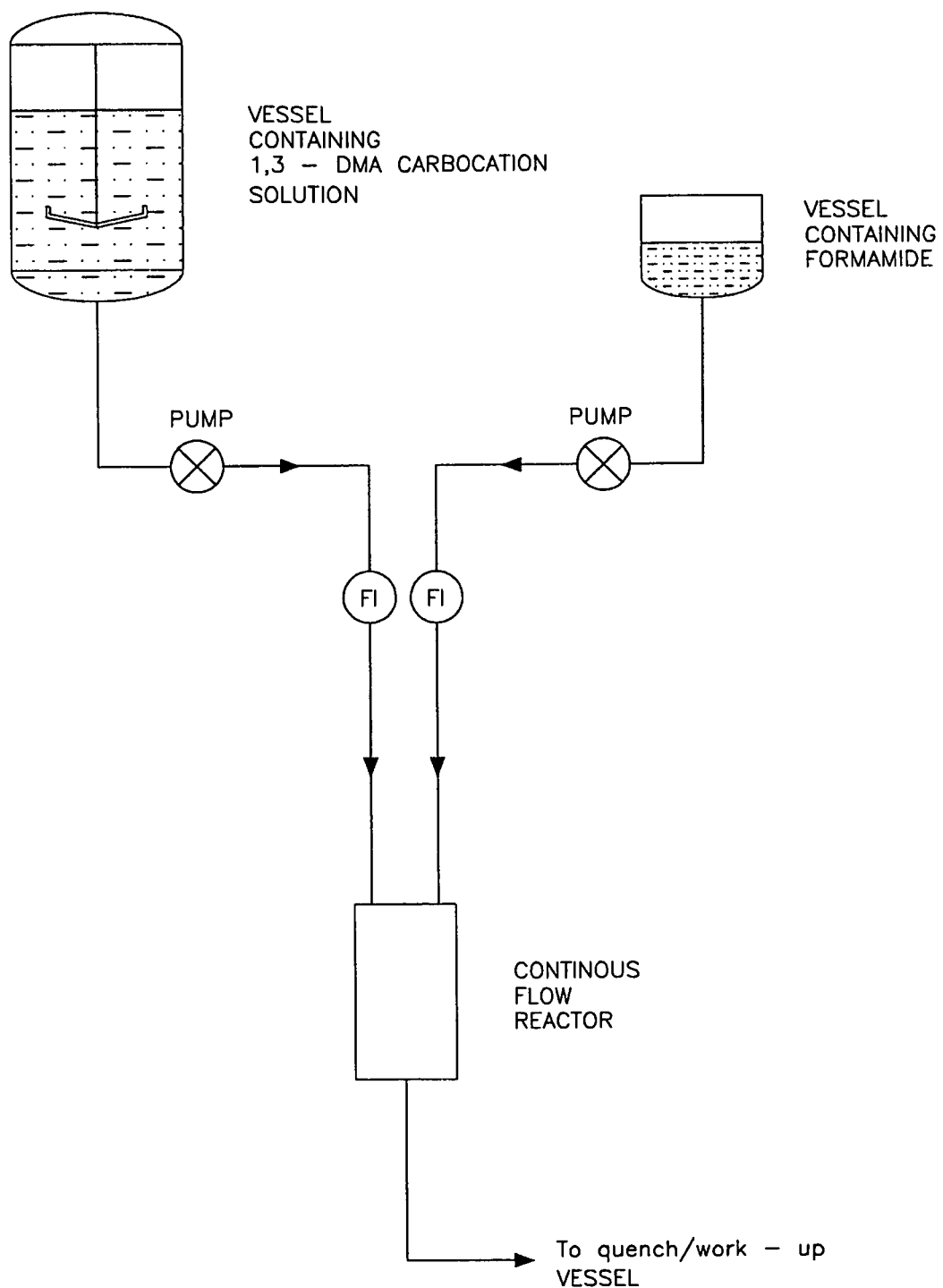
FIG. 2 shows an alternative embodiment, according to which the carbocation solution and the formamide are concurrently added to a continuous flow reactor.

Therefore, according to one embodiment of the invention, the mode of mixing is the concurrent or simultaneous adding of both the carbocation and the formamide into one common vessel. This concurrent or simultaneous adding can be accomplished either by in a batch-wise mode (as illustrated in FIG. 1) or in a continuous flow process (as illustrated in FIG. 2).

In the batch-wise mode, according to one embodiment of the invention, the time period for mixing/reacting is from 0.5 to 3 hours. In the batch-wise mode, in order to allow stirring from the very onset of the reaction, a sufficient amount of sulfuric acid might be present in the stirred mixing vessel before the two solutions are added.

The mode of concurrent/simultaneous mixing is advantageous as it allows keeping the carbocation-containing solution from step (a) well below the temperature at which the decomposition of the carbocation solution starts (above 60° C.).

Furthermore the concurrent/simultaneous mixing allows a nearly instant product formation thus avoiding or minimizing the formation of side products and/or decomposition due to global or local exothermic temperature spikes. Such a control may not be as relevant on the laboratory scale where rapid stirring is available and small overall amounts of chemicals are processed. However, this control is highly relevant for industrial scale production both from a quality and safety point of view.

Summary of the Relevant Effects

The process according to the present invention leads to a crude product comprising N-Formyl-1-amino-3,5-dimethyladamantane (NFORM) as an intermediate that is sufficiently pure to be transformed directly into Memantine hydrochloride, for example by means of simple hydrolysis with aqueous HCl, without any prior additional purification step(s).

Overall, the present invention provides an improved process for manufacturing N-Formyl-1-amino-3,5-dimethyladamantane starting from 1,3-dimethyladamantane that minimizes the use of hazardous chemicals.

The inventive process also minimizes the amount of waste and/or unused chemicals produced during the manufacture of Memantine or its intermediate products since large excess amounts of chemicals are avoided. This is achieved while improving selectivity and purity over the processes of the prior art without compromising the yield.

Furthermore, as opposed to the process of the prior art (WO 2007/101536) that works on the laboratory scale, the process according to the present invention is ready to be applied on an industrial scale, providing both high yield and high purity.

Converting the Intermediate Product NFORM into Memantine

In addition to manufacturing NFORM, the present invention also relates to converting the intermediate product NFORM into pharmaceutical grade Memantine. For this, a third step, namely step (c), i.e. a working-up step is required.

According to one embodiment of the invention, in order to achieve conversion, the intermediate N-Formyl-1-amino-3,5-dimethyladamantane in acid is diluted with water and extracted with a minimum amount of an appropriate solvent. According to a further embodiment of the invention, 1 to 6 volume parts solvent (as measured in ml) per weight part of 1,3-DMA (as measured in g) are used.

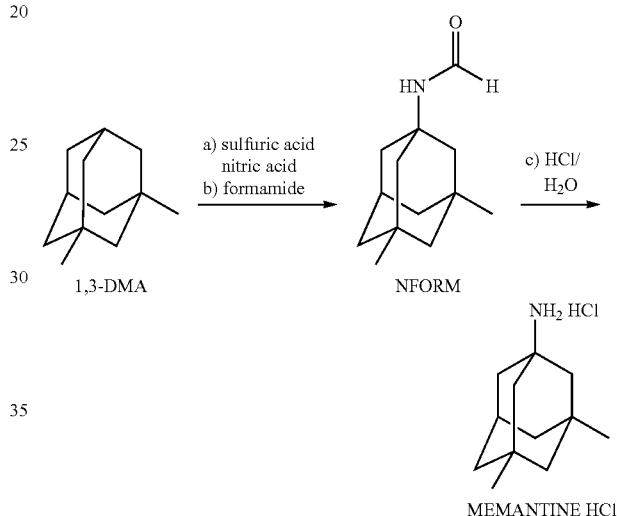

The "appropriate" solvent must be compatible with a strong acidic medium. Suitable solvents are halogenated solvents (e.g. dichloromethane), ethereal solvents, aliphatic or aromatic hydrocarbons. According to one embodiment of the invention, dichloromethane is used.

After washing, according to one embodiment of the invention, a solvent exchange from the organic solvent, in particular from dichloromethane into water is performed and the product can be hydrolyzed with aqueous hydrochloric acid to Memantine Hydrochloride. Neither an isolation of the intermediate nor a purification step is required in this inventive embodiment.

The final Memantine hydrochloride is obtained in a purity complying with the known "active pharmaceutical ingredient" (API) specifications. The process of the present invention in the scope of steps (a) and (b) or steps (a), (b) and (c) is feasible not only on a laboratory scale but has been proven to yield excellent results also when scaled-up to industrial manufacturing conditions.

In the following, the invention is further illustrated by means of non-limiting examples.

EXAMPLE 1

300 g (1.83 mol) of 1,3-dimethyladamantane (1,3-DMA) and 900 ml of sulfuric acid 96% (16.2 mol) are mixed and cooled to 0° C. to 5° C.

84 ml (1.20 mol) of nitric acid 65% are added under vigorous stirring over a time period of 4.5 hours, keeping the temperature between 0° C. to 5° C. Stirring is continued overnight at that temperature.

This solution is concurrently added together with 180 ml of formamide (4.53 mol) into a vessel precharged with sulfuric acid 96% (150 ml) preheated to 55-60° C., over the time period of two hours, keeping the internal temperature at T=55° C.-60° C.

After completion of the formylation, the mixture is cooled to 5° C. and quenched into a cold solution (0° C.), containing water (720 ml), aqueous ammonia 30% (480 ml) and dichloromethane (900 ml), while keeping the temperature below 25° C. The aqueous acidic layer is re-extracted with 450 ml of dichloromethane. The combined organic layers are washed three times with 600 ml water. With the last washing the pH is corrected to 8 to 9 using aqueous ammonia. N-Formyl-1-amino-3,5-dimethyladamantane is obtained as a solution in dichloromethane, which can be used in the subsequent step. Solvent removal gives 360 g of N-Formyl-1-amino-3,5-dimethyladamantane (NFORM) (yield 95%). The purity as measured by GC is 98%.

EXAMPLE 2

In this example, the hydrolysis of intermediate product NFORM as obtained according to the procedure described in Example 1 to Memantine HCl is described.

The solution of N-Formyl-1-amino-3,5-dimethyladamantane in dichloromethane is concentrated and water (1330 ml) is introduced. Hydrochloride acid 37% (990 g) is added and the mixture is heated to approximately 100° C. for 2 to 3 hours. A suspension is obtained. The reaction mixture is cooled to below 10° C., the product Memantine hydrochloride is isolated by filtration and washed with water and ethyl acetate. The wet product is dried under vacuum obtaining 320 g of Memantine HCl (overall molar yield 81%, purity 99.7%).

The invention claimed is:

1. A process for the manufacture of N-Formyl-1-amino-3,5-dimethyladamantane comprising the following steps:
   (a) reacting 1,3-dimethyladamantane with an acid mixture comprising concentrated sulfuric acid and concentrated nitric acid, wherein 1 to 6 volume parts of sulfuric acid as measured in ml are used per weight part of 1,3-dimethyladarnantane as measured in g;
   (b) reacting the solution from step (a) with an amount of formamide varying from 1 to 5 molar equivalents per mole of deprotonated 1,3-dimethyladamantane from step (a) to obtain N-Formyl-1-amino-3,5-dimethyladamantane;
   wherein in step (b), the molar ratio of total acid, i.e. the molar amount of sulfuric acid and the molar amount of nitric acid taken together versus the molar amount of formamide is at least 1.5.

2. The process of claim 1, wherein in step (b), the temperature is at least 50° C.

3. The process of claim 1, where the molar ratio of total acid i.e. the molar amount of sulfuric acid and the molar amount of nitric acid taken together versus the molar amount of formamide is in the range of 2:1 to 5:1.

4. The process of claim 1, wherein the concentrated sulfuric acid is present in a concentration range of 90 to 98% by weight or the concentrated nitric acid is present in a concentration range of 60 to 70% by weight, or both.

5. The process of claim 1, wherein step (a) is performed at temperatures from −10° C. to 50° C.

6. The process of claim 1, wherein in step (a), 3 to 5 volume parts of sulfuric acid as measured in ml are used per weight part of 1,3-dimethyladamantane as measured in g.

7. The process of claim 1, wherein the nitric acid in step (a) is used in a range from 0.5 to 2 molar equivalents or in a range from 0.6 to 0.8 molar equivalents of nitric acid relative to 1,3-dimethyladamantane.

8. The process of claim 1, wherein in step (b), 1.5 to 3 molar equivalents of formamide are employed per mole of deprotonated 1,3-dimethyladamantane from step (a).

9. The process of claim 1, wherein a temperature in the range of 50° C. to 65° C. is maintained for the reaction of step (b).

10. The process of claim 1, wherein the mode of mixing the two solutions in step (b) is the concurrent or simultaneous adding of both the carbocation solution from (a) and the formamide into a common reactor vessel over a given time period.

11. The process of claim 1, performed in a batch-wise mode.

12. The process of claim 1, performed in a continuous flow process.

13. The process of claim: 10, wherein the process is performed in batches of 100 kilograms or more.

14. A process for the manufacture of Memantine comprising the process of claim 1 for the manufacture of intermediate N-Formyl-1-amino-3,5-dimethyladamantane and further comprising the step of hydrolyzing said intermediate with aqueous hydrochloric acid to Memantine hydrochloride.

* * * * *

UNITED STATES PATENT AND TRADEMARK OFFICE
CERTIFICATE OF CORRECTION

PATENT NO. : 8,436,209 B2  
APPLICATION NO. : 12/736198  
DATED : May 7, 2013  
INVENTOR(S) : Florian Anton Martin Huber et al.

Page 1 of 1

It is certified that error appears in the above-identified patent and that said Letters Patent is hereby corrected as shown below:

Title Page, item 56, Foreign Patent Documents: "DE  10 2008 009279" should be
--DE 10 200<u>6</u> 009279--

Signed and Sealed this
Second Day of July, 2013

Teresa Stanek Rea
*Acting Director of the United States Patent and Trademark Office*